(12) United States Patent
Wheelock et al.

(10) Patent No.: US 8,152,341 B2
(45) Date of Patent: Apr. 10, 2012

(54) EXPANDABLE LIQUID VOLUME IN AN LED BULB

(75) Inventors: Glenn Wheelock, San Jose, CA (US); Bernhard Stonas, Hayward, CA (US)

(73) Assignee: Switch Bulb Company, Inc., San Jose, CA (US)

( * ) Notice: Subject to any disclaimer, the term of this patent is extended or adjusted under 35 U.S.C. 154(b) by 0 days.

(21) Appl. No.: 13/021,639

(22) Filed: Feb. 4, 2011

(65) Prior Publication Data

US 2012/0033440 A1  Feb. 9, 2012

(51) Int. Cl.
*F21V 29/00* (2006.01)
*F21V 3/00* (2006.01)
*H01R 33/22* (2006.01)

(52) U.S. Cl. ............ 362/373; 362/249.02; 362/311.02; 362/650

(58) Field of Classification Search ............. 362/218, 362/264, 294, 373, 580, 800, 96, 101, 154, 362/240, 249.02, 311.02, 318, 547, 555, 362/650

See application file for complete search history.

(56) References Cited

U.S. PATENT DOCUMENTS

| | | | |
|---|---|---|---|
| 5,890,794 A | | 4/1999 | Abtahi et al. |
| 5,927,094 A | * | 7/1999 | Nickum .................... 62/259.2 |
| 6,525,668 B1 | | 2/2003 | Petrick |
| 6,910,794 B2 | * | 6/2005 | Rice ............................ 362/547 |
| 7,637,636 B2 | | 12/2009 | Zheng et al. |
| 7,726,836 B2 | | 6/2010 | Chen |
| 7,922,359 B2 | | 4/2011 | Chiang |
| 7,922,363 B2 | | 4/2011 | Yang et al. |
| 8,047,680 B2 | | 11/2011 | Huang et al. |
| 8,092,045 B2 | | 1/2012 | Xiao et al. |
| 2004/0004435 A1 | | 1/2004 | Hsu |
| 2006/0176699 A1 | | 8/2006 | Crunk |
| 2006/0285331 A1 | * | 12/2006 | Wang et al. .................... 362/294 |
| 2007/0267976 A1 | * | 11/2007 | Bohler et al. ................ 315/112 |
| 2009/0052187 A1 | * | 2/2009 | Li ................................ 362/294 |
| 2009/0059594 A1 | * | 3/2009 | Lin ............................. 362/294 |
| 2009/0257220 A1 | * | 10/2009 | Lenk et al. .................... 362/186 |
| 2009/0302991 A1 | * | 12/2009 | Neilly et al. ................. 337/315 |
| 2010/0177519 A1 | * | 7/2010 | Schlitz ......................... 362/294 |

(Continued)

FOREIGN PATENT DOCUMENTS

WO  2004/100213 A2  11/2004

OTHER PUBLICATIONS

Non-Final Office Action received for U.S. Appl. No. 13/019,237, mailed on Jan. 30, 2012, 17 pages.

(Continued)

*Primary Examiner* — Alan Cariaso

(74) *Attorney, Agent, or Firm* — Morrison & Foerster LLP

(57) ABSTRACT

An LED bulb includes a base, a shell, a plurality of LEDs, a thermally conductive liquid, and a liquid-volume compensator mechanism. The shell is connected to the base. The plurality of LEDs is attached to the base and disposed within the shell. The thermally conductive liquid is held within the shell. The liquid-volume compensator mechanism is attached to the base. The liquid-volume compensator mechanism is configured to compensate for expansion of the thermally conductive liquid. The liquid-volume compensator mechanism moves from a first position to a second position. A first volume is provided for the thermally conductive liquid in the first position. A second volume, which is greater than the first volume, is provided for the thermally conductive liquid in the second position.

20 Claims, 9 Drawing Sheets

U.S. PATENT DOCUMENTS

| | | |
|---|---|---|
| 2010/0226137 A1 | 9/2010 | Xiao et al. |
| 2010/0246177 A1* | 9/2010 | Van De Ven ............. 362/249.02 |
| 2011/0050098 A1* | 3/2011 | Lenk et al. ..................... 315/32 |
| 2011/0193479 A1 | 8/2011 | Nilssen et al. |
| 2011/0305020 A1* | 12/2011 | Wang ....................... 362/249.02 |
| 2012/0002401 A1 | 1/2012 | Clifford |

OTHER PUBLICATIONS

Exxon Mobil Corporation, "Univolt 60 Material Safety Data Bulletin", Nov. 5, 2002, 9 pages.

* cited by examiner

EXPANDABLE LIQUID VOLUME IN AN LED BULB

BACKGROUND

1. Field

The present disclosure relates generally to liquid-cooled light-emitting diode (LED) bulbs and, more specifically, to providing an expandable volume in an LED bulb to allow for thermal expansion of a thermally conductive liquid.

2. Related Art

Traditionally, lighting has been generated using fluorescent and incandescent light bulbs. While both types of light bulbs have been reliably used, each suffers from certain drawbacks. For instance, incandescent bulbs tend to be inefficient, using only 2-3% of their power to produce light, while the remaining 97-98% of their power is lost as heat. Fluorescent bulbs, while more efficient than incandescent bulbs, do not produce the same warm light as that generated by incandescent bulbs. Additionally, there are health and environmental concerns regarding the mercury contained in fluorescent bulbs.

Thus, an alternative light source is desired. One such alternative is a bulb utilizing an LED. An LED comprises a semiconductor junction that emits light due to an electrical current flowing through the junction. Compared to a traditional incandescent bulb, an LED bulb is capable of producing more light using the same amount of power. Additionally, the operational life of an LED bulb is orders of magnitude longer than that of an incandescent bulb, for example, 10,000-100,000 hours as opposed to 1,000-2,000 hours.

While there are many advantages to using an LED bulb rather than an incandescent or fluorescent bulb, LEDs have a number of drawbacks that have prevented them from being as widely adopted as incandescent and fluorescent replacements. One drawback is that an LED, being a semiconductor, generally cannot be allowed to get hotter than approximately 120° C. As an example, A-type LED bulbs have been limited to very low power (i.e., less than approximately 8 W), producing insufficient illumination for incandescent or fluorescent replacements.

One potential solution to this problem is to use a large metallic heat sink attached to the LEDs and extending away from the bulb. However, this solution is undesirable because of the common perception that customers will not use a bulb that is shaped radically different from the traditionally shaped A-type form factor bulb. Additionally, the heat sink may make it difficult for the LED bulb to fit into pre-existing fixtures.

Another solution is to fill the bulb with a thermally conductive liquid to transfer heat from the LED to the shell of the bulb. The heat may then be transferred from the shell out into the air surrounding the bulb. As heat is transferred from the LED to the conductive liquid, the temperature of the liquid increases, resulting in an increase in the liquid volume due to thermal expansion. Some liquid-filled LED bulbs use a pocket of air or bubble in the bulb. As the temperature of the liquid increases, the volume of the liquid expands, and the pocket of air or bubble is compressed.

However, it is undesirable to have a pocket of air or bubble in the liquid-filled bulb. First, a pocket of air reduces the cooling efficiency of the bulb by creating an air barrier between the liquid and at least a portion of the outer shell housing. Second, the bubble may distort the light created by the LED, resulting in a non-uniform light distribution. The bubble may create a bright reflection or darkened area detracting from the visual appeal of the bulb. Third, an air bubble draws attention to the fact that the bulb is filled with a liquid, which may not be appealing to customers.

SUMMARY

In one exemplary embodiment, an LED bulb has a base, a shell connected to the base, a plurality of LEDs, a thermally conductive liquid, and a liquid-volume compensator mechanism. The plurality of LEDs is attached to the base and disposed within the shell. The thermally conductive liquid is held within the shell. The liquid-volume compensator mechanism is attached to the base. The liquid-volume compensator mechanism is configured to compensate for expansion of the thermally conductive liquid. The liquid-volume compensator mechanism moves from a first position to a second position. A first volume is provided for the thermally conductive liquid in the first position. A second volume, which is greater than the first volume, is provided for the thermally conductive liquid in the second position.

DETAILED DESCRIPTION

The following description is presented to enable a person of ordinary skill in the art to make and use the various embodiments. Descriptions of specific devices, techniques, and applications are provided only as examples. Various modifications to the examples described herein will be readily apparent to those of ordinary skill in the art, and the general principles defined herein may be applied to other examples and applications without departing from the spirit and scope of the various embodiments. Thus, the various embodiments are not intended to be limited to the examples described herein and shown, but are to be accorded the scope consistent with the claims.

Various embodiments are described below, relating to LED bulbs. As used herein, an "LED bulb" refers to any light-generating device (e.g., a lamp) in which at least one LED is used to generate the light. Thus, as used herein, an "LED bulb" does not include a light-generating device in which a filament is used to generate the light, such as a conventional incandescent light bulb. It should be recognized that the LED bulb may have various shapes in addition to the bulb-like A-type shape of a conventional incandescent light bulb. For example, the bulb may have a tubular shape, globe shape, or the like. The LED bulb of the present disclosure may further include any type of connector; for example, a screw-in base, a dual-prong connector, a standard two- or three-prong wall outlet plug, bayonet base, Edison Screw base, single pin base, multiple pin base, recessed base, flanged base, grooved base, side base, or the like.

As used herein, the term "liquid" refers to a substance capable of flowing. Also, the substance used as the thermally conductive liquid is a liquid or at the liquid state within, at least, the operating ambient temperature range of the bulb. An exemplary temperature range includes temperatures between −40° C. to +40° C. Also, as used herein, "passive convective flow" refers to the circulation of a liquid without the aid of a fan or other mechanical devices driving the flow of the thermally conductive liquid.

Figure 1:
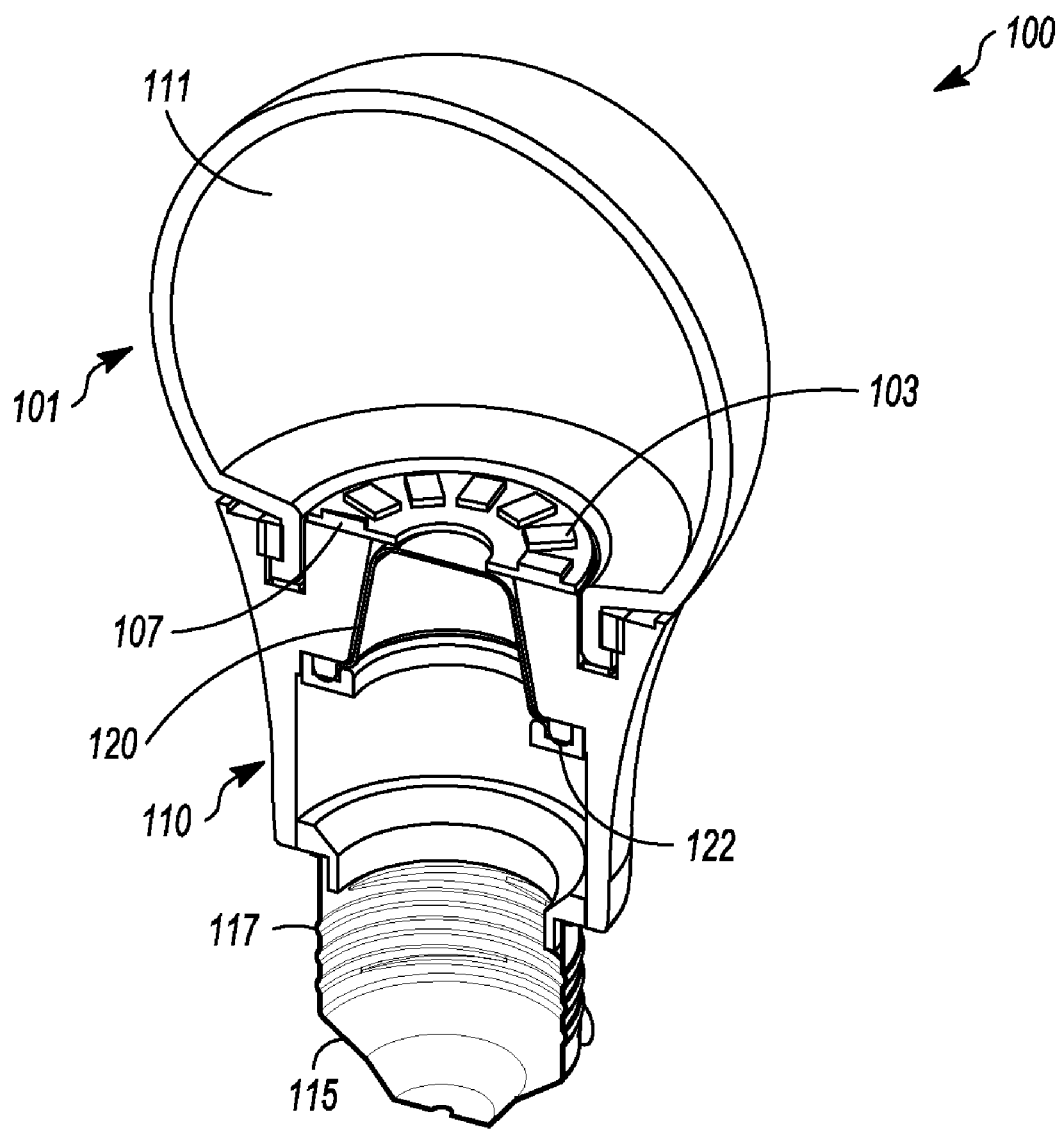
FIG. 1 depicts a cross-sectional view of an LED bulb with a diaphragm.

FIG. 1 illustrates a cross-sectional view of an exemplary LED bulb 100. LED bulb 100 includes a base 110 and a shell 101 encasing the various components of LED bulb 100. For convenience, all examples provided in the present disclosure describe and show LED bulb 100 being a standard A-type form factor bulb. However, as mentioned above, it should be appreciated that the present disclosure may be applied to LED bulbs having any shape, such as a tubular bulb, globe-shaped bulb, or the like.

Shell 101 may be made from any transparent or translucent material such as plastic, glass, polycarbonate, or the like. Shell 101 may include dispersion material spread throughout the shell to disperse light generated by LEDs 103. The dispersion material prevents LED bulb 100 from appearing to have one or more point sources of light.

In some embodiments, LED bulb 100 may use 6 W or more of electrical power to produce light equivalent to a 40 W incandescent bulb. In some embodiments, LED bulb 100 may use 20 W or more to produce light equivalent to or greater than a 75 W incandescent bulb. Depending on the efficiency of the LED bulb 100, between 4 W and 16 W of heat energy may be produced when the LED bulb 100 is illuminated.

The LED bulb 100 includes several components for dissipating the heat generated by LEDs 103. For example, as shown in FIG. 1, LED bulb 100 includes one or more LED mounts 107 for holding LEDs 103. LED mounts 107 may be made of any thermally conductive material, such as aluminum, copper, brass, magnesium, zinc, or the like. Since LED mounts 107 are formed of a thermally conductive material, heat generated by LEDs 103 may be conductively transferred to LED mounts 107. Thus, LED mounts 107 may act as a heat-sink or heat-spreader for LEDs 103.

LED mounts 107 are attached to bulb base 110, allowing the heat generated by LEDs 103 to be conducted to other portions of LED bulb 100. LED mounts 107 and bulb base 110 may be formed as one piece or multiple pieces. The bulb base 110 may also be made of a thermally conductive material and attached to LED mount 107 so that heat generated by LED 103 is conducted into the bulb base 110 in an efficient manner. Bulb base 110 is also attached to shell 101. Bulb base 110 can also thermally conduct with shell 101.

Bulb base 110 also includes one or more components that provide the structural features for mounting bulb shell 101 and LED mount 107. Components of the bulb base 110 include, for example, sealing gaskets, flanges, rings, adaptors, or the like. Bulb base 110 also includes a connector base 115 for connecting the bulb to a power source or lighting fixture. Bulb base 110 can also include one or more die-cast parts.

LED bulb 100 is filled with thermally conductive liquid 111 for transferring heat generated by LEDs 103 to shell 101. The thermally conductive liquid 111 fills the enclosed volume defined between shell 101 and bulb base 110, allowing the thermally conductive liquid 111 to thermally conduct with both the shell 101 and the bulb base 110. In some embodiments, the enclosed volume includes less than about 5 percent of gas when filled with the thermally conductive liquid 111. In some embodiments, thermally conductive liquid 111 is in direct contact with LEDs 103.

Thermally conductive liquid 111 may be any thermally conductive liquid, mineral oil, silicone oil, glycols (PAGs), fluorocarbons, or other material capable of flowing. It may be desirable to have the liquid chosen be a non-corrosive dielectric. Selecting such a liquid can reduce the likelihood that the liquid will cause electrical shorts and reduce damage done to the components of LED bulb 100.

LED bulb 100 includes a liquid-volume compensator mechanism to facilitate thermal expansion of thermally conductive liquid 111 contained in the LED bulb 100. In the exemplary embodiment depicted in FIG. 1, the liquid-volume compensator mechanism includes diaphragm element 120 for providing an expandable liquid volume. Diaphragm element 120 is a flexible membrane that is chemically compatible with thermally conductive liquid 111. Diaphragm element 120 may be made of an elastomer or synthetic rubber, such as Viton. Other suitable materials include silicone, fluorosilicone, fluorocarbon, Nitrile rubber, or the like. While the present embodiment of a liquid-volume compensator mechanism includes a diaphragm element 120, one skilled in the art would recognize that a liquid-volume compensator mechanism could be made from other elements, such as a disk, piston, vane, plunger, slide, closed cell foam, bellow, or the like.

In the present exemplary embodiment, diaphragm element 120 is attached to bulb base 110 to create a substantially impermeable seal. For example, the perimeter of diaphragm element 120 may be clamped to a flange or seat feature of the bulb base 110. As shown in FIG. 1, diaphragm element 120 includes a sealing bead 122 to improve sealing characteristics. While FIG. 1 depicts one possible sealing configuration, one skilled in the art would recognize that other sealing techniques could be used.

In FIG. 1, diaphragm element 120 is attached to bulb base 110 to allow diaphragm element 120 to function as a liquid-volume compensator mechanism. For example, as LEDs 103 produce heat, the thermally conductive liquid 111 expands, increasing the pressure inside the enclosed volume defined between shell 101 and bulb base 110. As shown in FIG. 1, at least a portion of one surface of diaphragm element 120 is in fluidic connection to the thermally conductive liquid 111 such that the liquid pressure exerts a force on at least part of diaphragm element 120. Diaphragm element 120 is able to deflect from a first position to a second position, in response to the increase in liquid pressure resulting from the volume of the thermally conductive fluid expanding from a first volume to a second volume.

The size and shape of diaphragm element 120 are selected to provide a liquid-volume compensator mechanism with an expandable volume ($V_e$). The size of the expandable volume ($V_e$) depends on several parameters, including total liquid volume ($V_f$), the lowest average fluid temperature ($T_a$), highest average bulb temperature ($T_b$), and coefficient of thermal expansion ($\alpha$). The minimum capacity of the expandable volume ($V_{e(min)}$) can be calculated as:

$$V_{e(min)} = V_f \times \alpha (T_b - T_a).$$ (Equation 1)

$V_f$ is the total liquid volume at the lowest average fluid temperature ($T_a$) that is approximately the volume of thermally conductive liquid 111 as installed in the LED bulb 100 during manufacturing. Exemplary ranges for $V_f$ at 25° C. include a range of 15 to 90 ml and a preferred range of 40 to 60 ml. α is the coefficient of thermal expansion, which is a material property of the thermally conductive liquid 111. α can be selected to minimize or reduce the expandable volume ($V_e$). An exemplary range of α includes $1.3 \times 10^{-3}$ °C.$^{-1}$ to $8 \times 10^0$ C.$^{-1}$.

$T_a$ and $T_b$ are based on estimated environmental conditions and maximum operating temperature of the LEDs 103. Using Equation 1 to calculate $V_e$ of the liquid-volume compensator mechanism, the lowest expected $T_a$ should be used. An exemplary range for $T_a$ includes −40° C. to +40° C. $T_b$ is the average, steady-state temperature of the thermally conductive liquid 111 when the LED bulb 100 is operating at full power. An exemplary $T_b$ is approximately 90° C. Preferably, $T_b$ should be below 120° C. The LED bulb can reach steady-state temperature after 180 minutes of continuous operation.

In the present exemplary embodiment, the liquid-volume compensator mechanism (e.g., diaphragm element 120) provides a $V_e$ that is slightly larger than $V_{e(min)}$ calculated using Equation 1. An exemplary $V_e$ of the liquid-volume compensator mechanism is at least 5 ml. Another exemplary $V_e$ of the liquid-volume compensator mechanism is at least 7 ml.

As shown in FIG. 1, in the present exemplary embodiment, an opening is provided at the center of the LEDs 103 so that thermally conductive liquid 111 is in fluidic connection with at least a portion of diaphragm element 120. A relatively smaller opening has the advantage of reducing the amount of light absorbed by diaphragm element 120. For example, the opening can be less than 5 mm but larger than 1 mm in diameter. To reduce the light absorbed by diaphragm element 120, the opening may be covered with a perforated plate or screen. The opening can also be covered with a reflective baffle.

As noted above, light bulbs typically conform to a standard form factor, which allows bulb interchangeability between different lighting fixtures and appliances. Accordingly, in the present exemplary embodiment, LED bulb 100 includes connector base 115 for connecting the bulb to a lighting fixture. In one example, connector base 115 may be a conventional light bulb base having threads 117 for insertion into a conventional light socket. However, as noted above, it should be appreciated that connector base 115 may be any type of connector for mounting LED bulb 100 or coupling to a power source. For example, connector base may provide mounting via a screw-in base, a dual-prong connector, a standard two- or three-prong wall outlet plug, bayonet base, Edison Screw base, single pin base, multiple pin base, recessed base, flanged base, grooved base, side base, or the like.

Figure 2A:
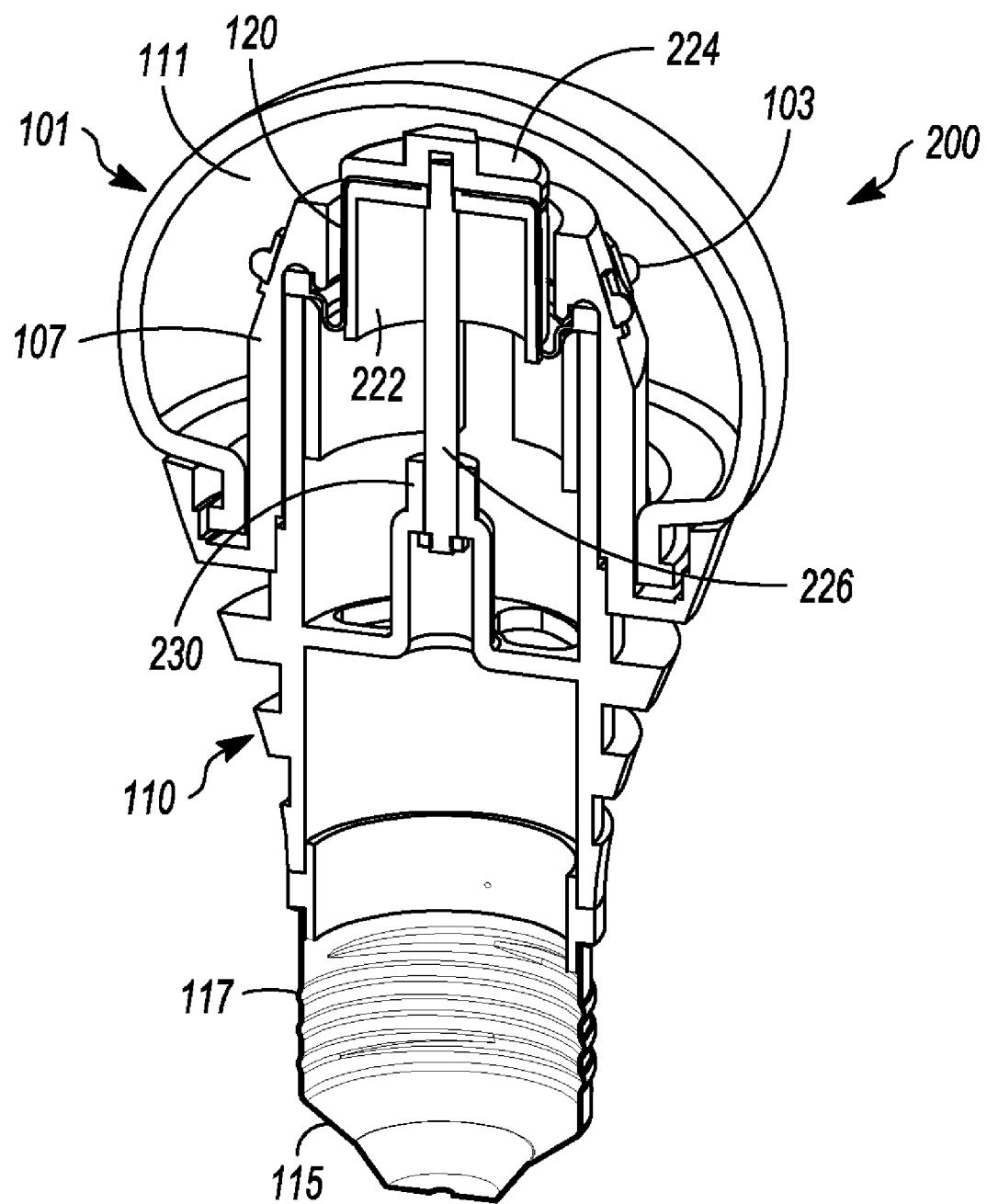
FIG. 2A depicts a cross-sectional view of an LED bulb with a diaphragm and piston in extended position.

FIG. 2A depicts a cross-sectional view of LED bulb 200 with an array of LEDs 103 that are mounted in an outward orientation to improve light distribution. As shown in FIG. 2A, the LEDs 103 are also directed away from the liquid-volume compensator mechanism, reducing shadows or dark regions created by exposed portions of the liquid-volume compensator mechanism. FIG. 2A depicts a centrally located liquid-volume compensator mechanism including a diaphragm element 120 attached to piston 222 and cap 224 using guide rod 226 as a threaded fastener. In the present exemplary embodiment, diaphragm element 120 is clamped between piston 222 and cap 224 to create a substantially impermeable seal. The perimeter of diaphragm element 120 may also be clamped to bulb base 110 to create a substantially impermeable seal.

As described above, LEDs 103 produce heat, and the thermally conductive liquid 111 expands, increasing the pressure inside the enclosed volume created between shell 101 and bulb base 110. The liquid-volume compensator mechanism is exposed to the thermally conductive liquid 111 so that the liquid pressure exerts a force on one or more of the parts of the liquid-volume compensator mechanism. In the embodiment depicted in FIG. 2A, the liquid pressure exerts a force on the diaphragm element 120 and cap 224.

The liquid-volume compensator mechanism is able to deflect or deform in response to the increase in pressure resulting in an increased volume. In FIG. 2A, the sidewall of diaphragm element 120 is able to roll or fold as diaphragm element 120 is deflected. Sufficient clearance is provided between bulb base 110 and piston 222 to allow the sidewall of diaphragm element 120 to fold or roll. Diaphragm element 120 can have sidewalls that are tapered or crowned. Diaphragm element 120 can also have sidewalls that are substantially cylindrical.

Figure 2B:
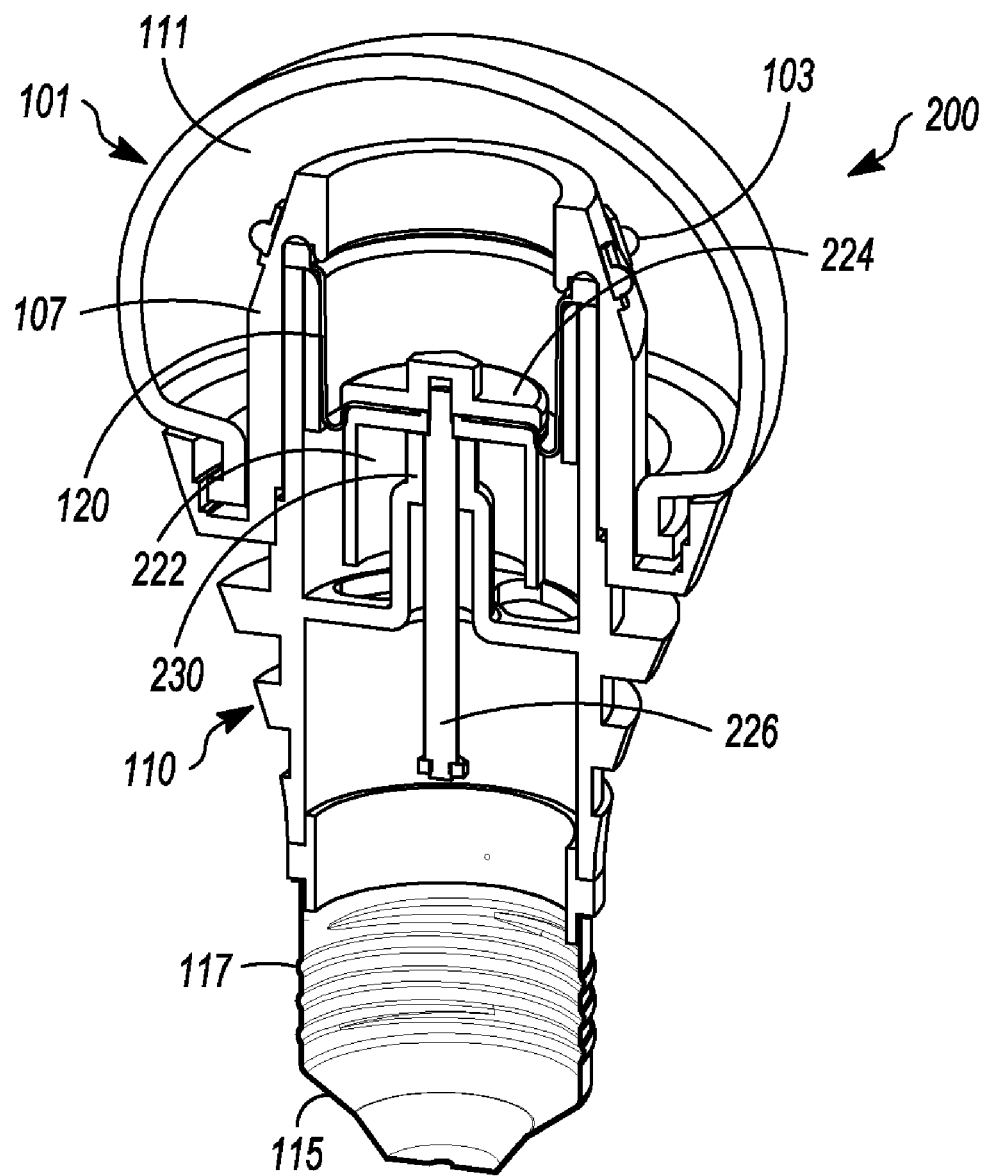
FIG. 2B depicts a cross-sectional view of an LED bulb with a diaphragm and piston in retracted position.

FIG. 2A depicts a liquid-volume compensator mechanism (e.g., diaphragm element 120, piston 222, cap 224, and guide rod 226) in an extended position. FIG. 2B depicts LED bulb 200 with the liquid-volume compensator mechanism in a retracted position. The liquid-volume compensator mechanism moves between an extended position and a retracted position to provide an increase in liquid volume capacity of the LED bulb 200 due to thermal expansion of thermally conductive liquid 111. For example, the extended position may represent the position of the liquid-volume compensator mechanism when the thermally conductive liquid 111 is cool (e.g., bulb is not in operation). The retracted position may represent the position of the liquid-volume compensator mechanism when the thermally conductive liquid 111 is warm (e.g., bulb is in operation and has reached a steady-state temperature).

In FIG. 2A, piston 222 provides support for diaphragm element 120 to prevent collapse or buckling of the diaphragm walls. Piston 222 can also include piston sidewalls that are at least as long as the sidewalls of diaphragm element 120. Guide rod 226 slides through guide bore 230 to allow axial movement of the diaphragm element 120, piston 222, and cap 224. Guide rod 226 may be made of stainless steel, brass, bronze, aluminum, or the like. In the present exemplary embodiment, guide rod 226 and guide bore 230 are of different materials to prevent galling or seizure. Alternatively, guide bore 230 is a sleeve or insert made of a material that is different from the material of bulb base 110.

Figure 3A:
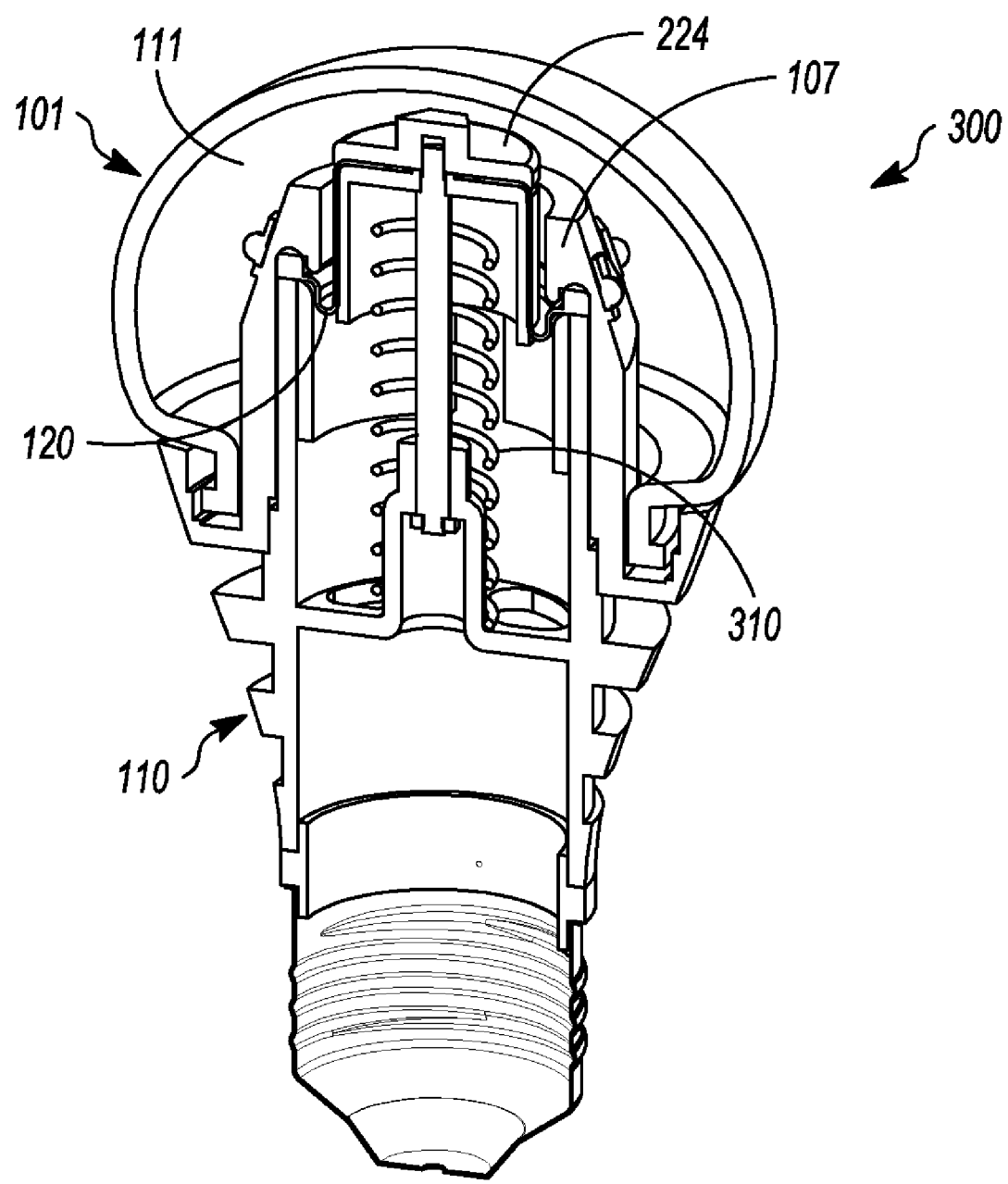
FIG. 3A depicts a cross-sectional view of an LED bulb with a diaphragm, piston, and return spring in extended position.

FIG. 3A depicts a cross-sectional view of LED bulb 300, including a liquid-volume compensator mechanism with a spring-loaded piston to provide a positive pressure in thermally conductive liquid 111. A positive pressure can be maintained inside the bulb to improve the liquid-to-air seal between shell 101 and bulb base 110. By maintaining a positive pressure in the thermally conductive liquid 111, the seal provides a liquid-impermeable barrier, preventing the liquid from leaking out. However, it is not necessary that the seal be air-impermeable, as the positive liquid pressure prevents air from being drawn into LED bulb 300 (e.g., by vacuum). In general, providing a liquid-impermeable seal is more practical and cost-effective than providing an air-impermeable seal. Thus, an LED bulb with a pressurized, thermally conductive liquid 111 offers improved sealing characteristics.

Return spring 310 may also be selected to provide a force that is sufficient to overcome friction in the liquid-volume compensator mechanism. For example, a positive force may be required to restore the shape of diaphragm element 120 corresponding to an extended position of the liquid-volume compensator mechanism. Return spring 310 can be selected so that a maximum liquid pressure is not exceeded when return spring 310 is compressed.

In FIG. 3A, the liquid-volume compensator mechanism includes a diaphragm element 120 attached to piston 222 (FIG. 2A) and cap 224 using guide rod 226 (FIG. 2A) as a threaded fastener. As shown in FIG. 3A, return spring 310 is a wound compression spring mounted between piston 222 (FIG. 2A) and a flange or seat in bulb base 110. A sealed air chamber in bulb base 110 may be provided to provide a return force. In some embodiments, an extension spring, torsional spring, polymer spring, or the like is used to provide a return force.

Figure 3B:
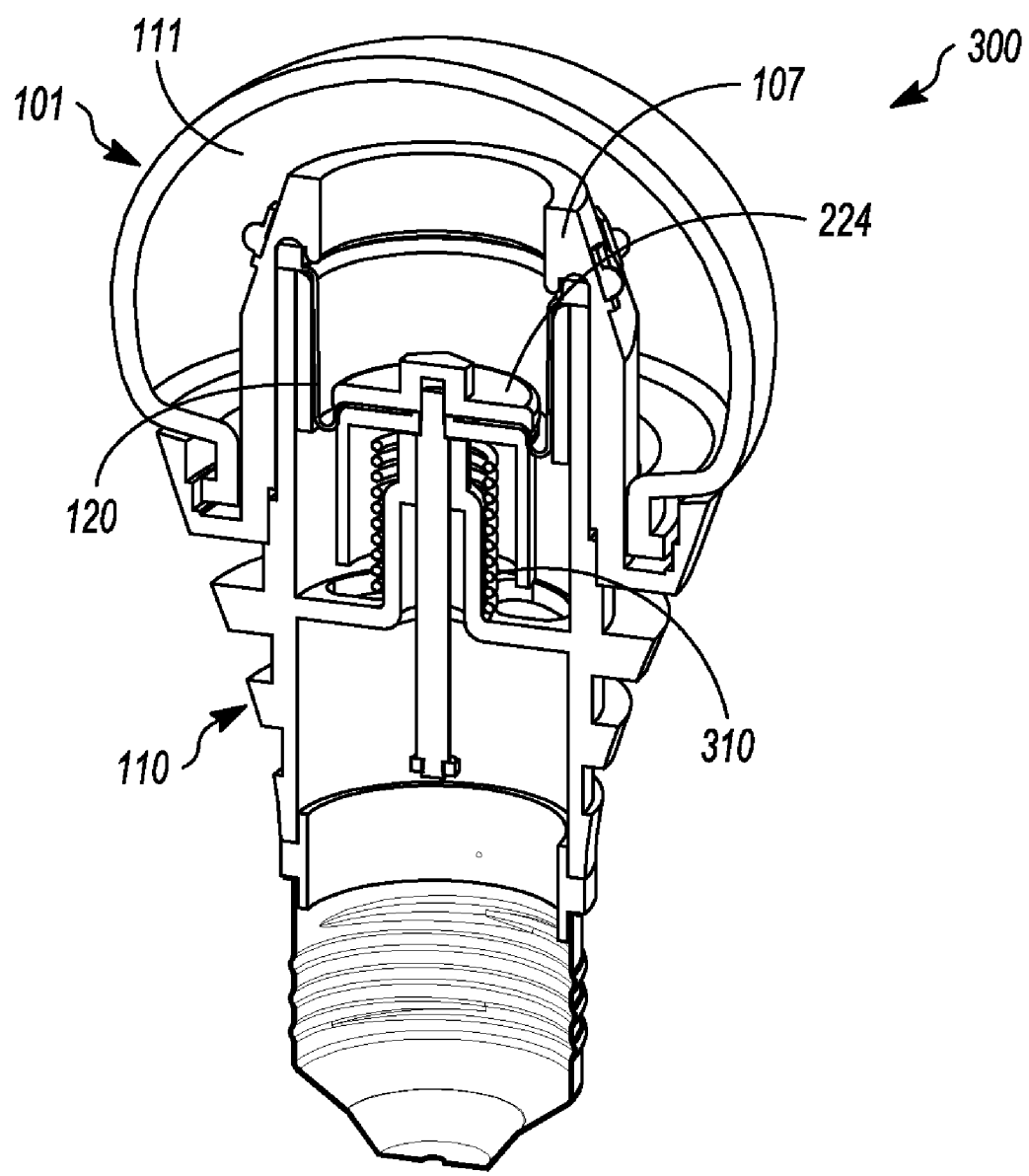
FIG. 3B depicts a cross-sectional view of an LED bulb with a diaphragm, piston, and return spring in retracted position.

FIG. 3A depicts the liquid-volume compensator mechanism in an extended position. FIG. 3B depicts LED bulb 300 with the liquid-volume compensator mechanism in a retracted position. As depicted in FIG. 3B, in the retracted position, return spring 310 is compressed.

Figure 4A:
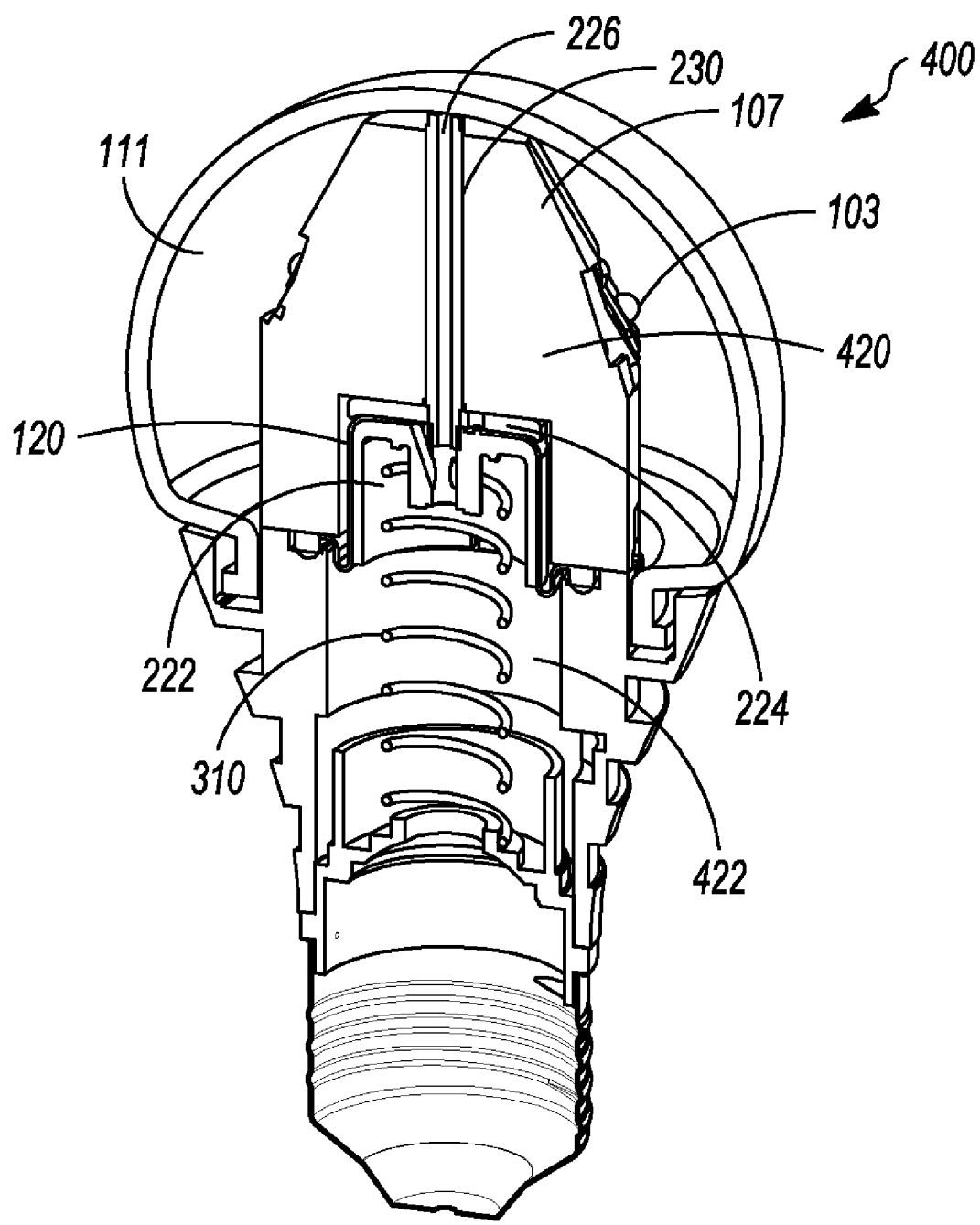
FIG. 4A depicts a cross-sectional view of an LED bulb with a shrouded diaphragm, piston, return spring, and inverted rod in extended position.

FIG. 4A depicts a cross-sectional view of an exemplary LED bulb 400 with a center protrusion 420 for shrouding the liquid-volume compensator mechanism. By shrouding the liquid-volume compensator mechanism, protrusion 420 prevents the mechanism from interfering with light distribution. For example, protrusion 420 may have a surface finish to reduce the amount of light absorbed by the protrusion 420. Consequently, protrusion 420 will absorb less light than would an unshrouded or exposed liquid-volume compensator mechanism. Also, it is advantageous that the center protrusion be located in LED bulb 400 so that it does not block light emitted from LEDs 103.

By shrouding the liquid-volume compensator mechanism, protrusion 420 prevents the mechanism from interfering with convective liquid flow within the LED bulb 400. Consequently, the outside surface of protrusion 420 facilitates convective flow of thermally conductive liquid 111. Protrusion 420 may also include tapered and rounded corners such that currents in the thermally conductive liquid 111 are able to follow a passive convective flow. The shape of protrusion 420 should minimize stagnant or dead zones in the convective flow of thermally conductive liquid 111. For example, protrusion 420 can be shaped to facilitate convection of thermally conductive liquid 111 when LED bulb 400 is in different orientations.

Protrusion 420 may also facilitate heat conduction into thermally conductive liquid 111 by providing additional surface area. Heat produced by LEDs 103 is conducted through LED mount 107 to protrusion 420, and then conducted from protrusion 420 to thermally conductive liquid 111.

In the present embodiment, LED mount 107 includes the protrusion 420 to partially enclose cavity 422 containing the liquid-volume compensator mechanism. The liquid-volume compensator mechanism depicted in FIG. 4A includes diaphragm element 120, piston 222, cap 224, guide rod 226, and return spring 310. As shown in FIG. 4A, one end of guide rod 226 extends toward the shell. The center protrusion 420 includes guide bore 230 allowing the liquid-volume compensator mechanism to move in an axial direction. By orienting the guide rod 226 toward the shell, the liquid-volume compensator mechanism can be partially located in the enclosed volume of LED bulb 400 without creating a large obstruction. Placing the liquid-volume compensator mechanism partially within the enclosed volume allows the size of the bulb base to be reduced.

As shown in FIG. 4A, protrusion 420 and LED mount 107 are made from the same part. However, protrusion 420 may be a separate part or may be made from the same part as the bulb base. Protrusion 420 may include one or more liquid paths to allow flow of thermally conductive liquid 111 into and out of cavity 422.

In FIG. 4A, as the LEDs 103 generate heat, the thermally conductive liquid 111 exerts a force on the end of guide rod 226, which is connected to diaphragm element 120 via piston 222 and cap 224. Thermally conductive liquid 111 can also exert a force on other parts that are attached to diaphragm element 120, such as piston 222 and cap 224.

Diaphragm element 120 is able to deflect or deform in response to the increase in pressure resulting in an increased volume. In FIG. 4A, the sidewall of diaphragm element 120 is able to roll or fold as diaphragm element 120 is deflected. Sufficient clearance is provided between cavity 422 and piston 222 to allow diaphragm element 120 to fold or roll.

Figure 4B:
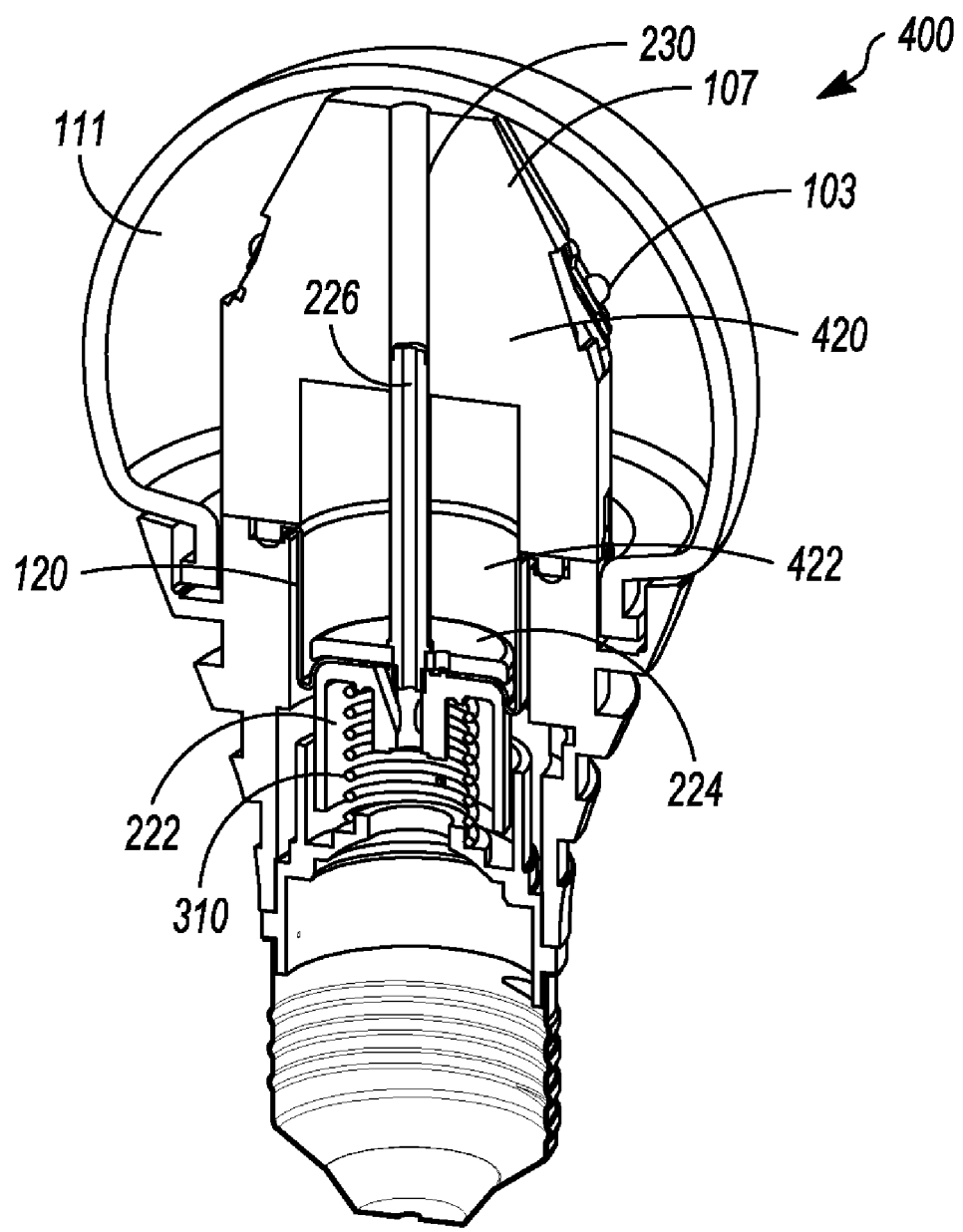
FIG. 4B depicts a cross-sectional view of an LED bulb with a shrouded diaphragm, piston, return spring, and inverted rod in retracted position.

FIG. 4A depicts the liquid-volume compensator mechanism in an extended position. FIG. 4B depicts LED bulb 400 with the liquid-volume compensator mechanism in a retracted position. As depicted in FIG. 4B, in the retracted position, return spring 310 is compressed.

In FIG. 4A, LED bulb 400 also includes a feature for limiting the inward stroke of the liquid-volume compensator mechanism. For example, protrusion 420 may include a stroke-limiting feature, such as a seat or flange that prevents cap 224 from moving past an extension position. In embodiments that include return spring 310, a stroke-limiting feature is desirable to prevent the sidewalls of diaphragm element 120 from being loaded by the return force. Thus, in one exemplary embodiment, the stroke of the diaphragm element 120 should be slightly larger than what is allowed by the stroke-limiting feature.

Figure 5A:
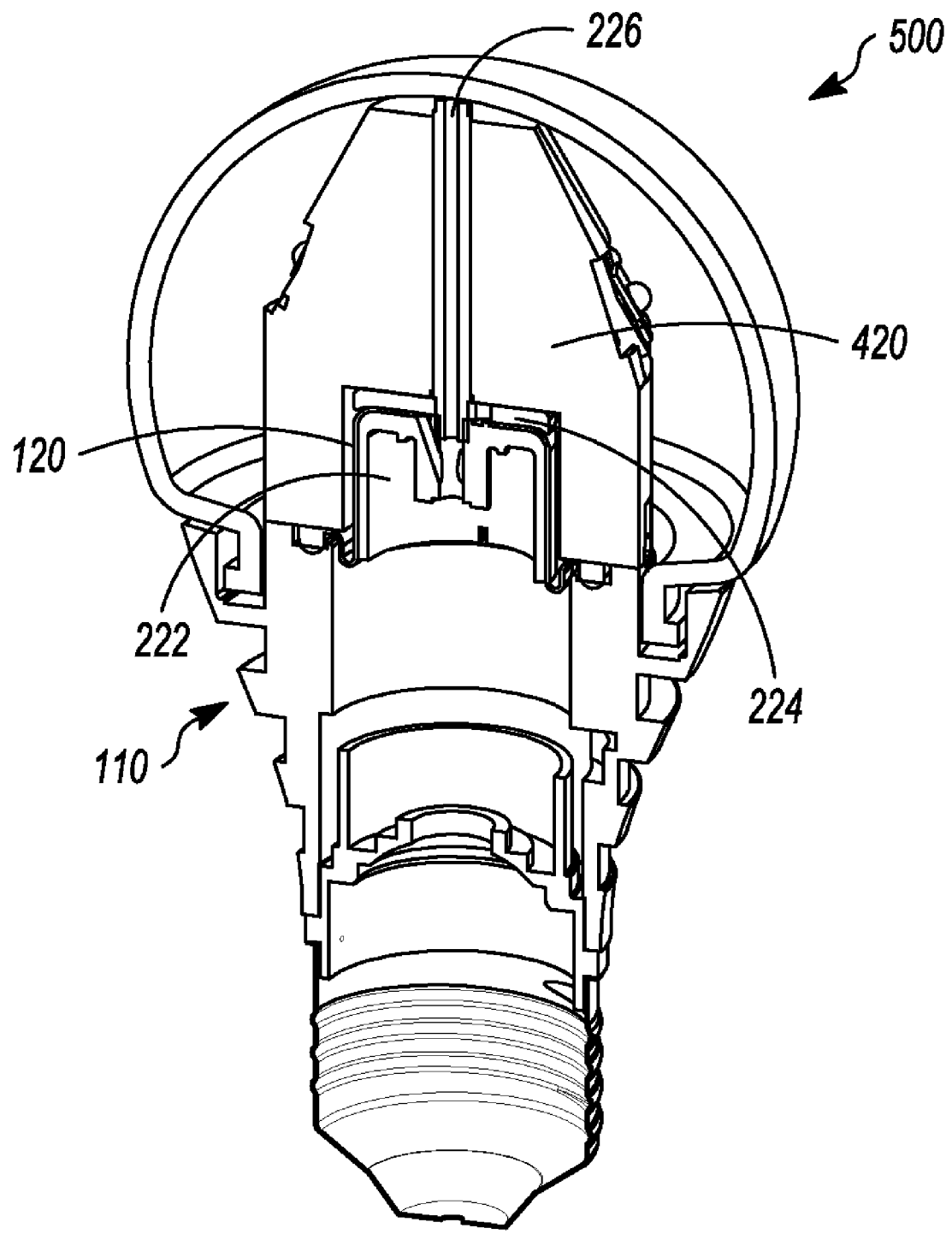
FIG. 5A depicts a cross-sectional view of an LED bulb with a shrouded diaphragm, piston, and inverted rod in extended position.
Figure 5B:
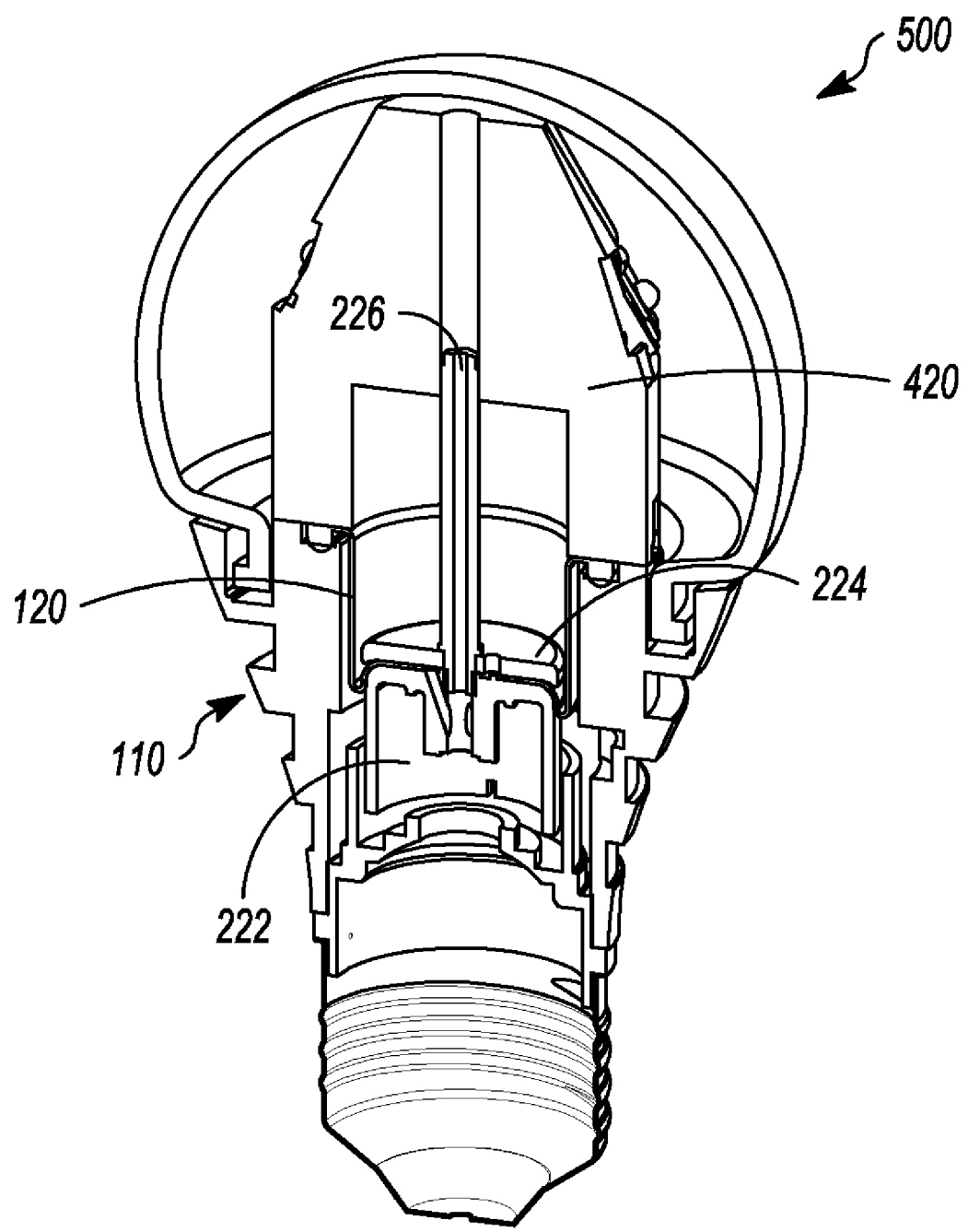
FIG. 5B depicts a cross-sectional view of an LED bulb with a shrouded diaphragm, piston, and inverted rod in retracted position.

FIG. 5A depicts a cross-sectional view of an exemplary LED bulb 500 with center protrusion 420 and a liquid-volume compensator mechanism. The liquid-volume compensator mechanism depicted in FIG. 5A includes diaphragm element 120, piston 222, cap 224, and guide rod 226. In the embodiment depicted in FIG. 5A, a sealed air chamber in bulb base 110 may be provided to provide a return force such that the piston works without a return spring. In this embodiment, the piston retracts as the fluid expands with heat and extends as the fluid contracts as it cools. FIG. 5A depicts the liquid-volume compensator mechanism in an extended position. FIG. 5B depicts LED bulb 500 with the liquid-volume compensator mechanism in a retracted position.

The diameter and stroke of the liquid-volume compensator mechanism are configured to reduce the size of the bulb base. For example, the diameter of the liquid-volume compensator mechanism is reduced and the stroke increased to provide a narrower bulb base. Also, a thermally conductive liquid with a reduced thermal expansion can be selected, allowing for a reduction in the expandable volume capacity and the size of the liquid-volume compensator mechanism.

Although a feature may appear to be described in connection with a particular embodiment, one skilled in the art would recognize that various features of the described embodiments may be combined. Moreover, aspects described in connection with an embodiment may stand alone.

We claim:
1. A liquid-cooled light-emitting diode (LED) bulb comprising:
 a base;
 a shell connected to the base;
 a plurality of LEDs attached to the base and disposed within the shell;

a thermally conductive liquid held within the shell, wherein the LEDs are immersed in the thermally conductive liquid to transfer heat from the LEDs to the shell; and a liquid-volume compensator mechanism disposed within the LED bulb,
   wherein the liquid-volume compensator mechanism is configured to compensate for expansion of the thermally conductive liquid,
   wherein the liquid-volume compensator mechanism moves from a first position to a second position,
   wherein a first volume is provided for the thermally conductive liquid in the first position, and
   wherein a second volume, which is greater than the first volume, is provided for the thermally conductive liquid in the second position.

2. The liquid-cooled LED bulb of claim 1, wherein the thermally conductive liquid fills a volume defined within the shell and base, and wherein the volume includes less than about 5 percent of a gas.

3. The liquid-cooled LED bulb of claim 2, wherein the volume contains between 15 and 90 milliliters of thermally conductive liquid.

4. The liquid-cooled LED bulb of claim 1, wherein the second volume is at least 7 milliliters.

5. The liquid-cooled LED bulb of claim 1, wherein the liquid-volume compensator mechanism comprises:
   a flexible diaphragm connected to the base.

6. The liquid-cooled LED bulb of claim 5, wherein the liquid-volume compensator mechanism further comprises:
   a piston connected to the flexible diaphragm;
   a rod having a first end, a second end, and a shaft, the first end of the rod affixed to the center of the piston; and
   a rod guide surrounding a portion of the shaft of the rod, the rod guide configured to allow movement of the rod in an axial direction.

7. The liquid-cooled LED bulb of claim 6, wherein the second end of the rod extends toward the shell.

8. The liquid-cooled LED bulb of claim 6, wherein the second end of the rod extends away from the shell.

9. The liquid-cooled LED bulb of claim 6, further comprising:
   a spring element configured to apply a return force on one face of the diaphragm element.

10. The liquid-cooled LED bulb of claim 1, wherein the thermally conductive liquid has a rate of thermal expansion between $1.3\times10^{-3}$° and $8\times10^{-4}$° Celsius$^{-1}$.

11. The liquid-cooled LED bulb of claim 1, further comprising:
   an LED mount, wherein the LEDs are disposed on the LED mount.

12. The liquid-cooled LED bulb of claim 11, wherein the LEDs are disposed on the LED mount in a radial pattern.

13. The liquid-cooled LED bulb of claim 1, wherein the base comprises:
   a heat-spreader base thermally connected to the LEDs, wherein the heat-spreader base is configured to conductively transfer heat from the LEDs.

14. The liquid-cooled LED bulb of claim 1, wherein at least a portion of the thermally conductive liquid is disposed in the optical path from the LEDs to the shell.

15. A liquid-cooled light-emitting diode (LED) bulb comprising:
   a shell;
   a plurality of LEDs disposed within the shell;
   a thermally conductive liquid held within the shell, wherein the LEDs are immersed in the thermally conductive liquid to transfer heat from the LEDs to the shell; and
   a liquid-volume compensator mechanism configured to compensate for expansion of the thermally conductive liquid from a first volume to a second volume, the liquid-volume compensator mechanism comprising:
      a flexible diaphragm;
      a piston connected to the flexible diaphragm;
      a rod having a first end, a second end, and a shaft, the first end of the rod affixed to the center of the piston; and
      a rod guide surrounding a portion of the shaft of the rod, the rod guide configured to allow movement of the rod in an axial direction.

16. The liquid-cooled LED bulb of claim 15, wherein the thermally conductive liquid fills a volume defined within the shell, and wherein the volume includes less than about 5 percent of a gas.

17. The liquid-cooled LED bulb of claim 15, further comprising:
   an LED mount, wherein the LEDs are disposed in a radial pattern on the LED mount.

18. The liquid-cooled LED bulb of claim 15, wherein the base comprises:
   a heat-spreader base thermally connected to the LEDs, wherein the heat-spreader base is configured to conductively transfer heat from the LEDs.

19. The liquid-cooled LED bulb of claim 15, wherein at least a portion of the thermally conductive liquid is disposed in the optical path from the LEDs to the shell.

20. A method of making a liquid-cooled light-emitting diode (LED) bulb comprising:
   obtaining a base;
   connecting a shell to the base;
   connecting a plurality of LEDs to the base and disposed within the shell;
   filling the shell with a thermally conductive liquid, wherein the LEDs are immersed in the thermally conductive liquid to transfer heat from the LEDs to the shell; and
   providing a liquid-volume compensator mechanism within the LED bulb,
      wherein the liquid-volume compensator mechanism is configured to compensate for expansion of the thermally conductive liquid,
      wherein the liquid-volume compensator mechanism moves from a first position to a second position,
      wherein a first volume is provided for the thermally conductive liquid in the first position, and
      wherein a second volume, which is greater than the first volume, is provided for the thermally conductive liquid in the second position.

* * * * *

UNITED STATES PATENT AND TRADEMARK OFFICE
CERTIFICATE OF CORRECTION

PATENT NO. : 8,152,341 B2
APPLICATION NO. : 13/021639
DATED : April 10, 2012
INVENTOR(S) : Glenn Wheelock et al.

It is certified that error appears in the above-identified patent and that said Letters Patent is hereby corrected as shown below:

At column 5, line number 10, Delete "$8 \times 10° C.^{-1}$" and insert --$8 \times 10^{-4} ° C.^{-1}$--, therefor.

Signed and Sealed this
Twenty-ninth Day of May, 2012

David J. Kappos
*Director of the United States Patent and Trademark Office*